(12) United States Patent
Zheng et al.

(10) Patent No.: US 12,740,829 B2
(45) Date of Patent: Sep. 22, 2026

(54) SYSTEMS AND METHODS FOR SURGICAL TASK AUTOMATION

(71) Applicant: Shanghai United Imaging Intelligence Co., Ltd., Shanghai (CN)

(72) Inventors: Meng Zheng, Cambridge, MA (US); Benjamin Planche, Briarwood, NY (US); Ziyan Wu, Lexington, MA (US); Terrence Chen, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 1014 days.

(21) Appl. No.: 17/955,279

(22) Filed: Sep. 28, 2022

(65) Prior Publication Data

US 2024/0099774 A1 Mar. 28, 2024

(51) Int. Cl.

*A61B 34/10* (2016.01)
*A61B 34/30* (2016.01)
*G06T 17/20* (2006.01)
*G16H 50/50* (2018.01)

(52) U.S. Cl.

CPC .............. *A61B 34/10* (2016.02); *A61B 34/30* (2016.02); *G06T 17/20* (2013.01); *G16H 50/50* (2018.01); *A61B 2034/105* (2016.02); *A61B 2034/107* (2016.02)

(58) Field of Classification Search

CPC ......... A61B 34/10; A61B 34/30; G06T 17/20; G16H 50/50

See application file for complete search history.

(56) References Cited

U.S. PATENT DOCUMENTS 6,913,603 B2 7/2005 Knopp et al.
9,220,570 B2 12/2015 Kim et al.
2018/0008351 A1* 1/2018 Schoenefeld .......... A61B 17/15
2018/0325526 A1* 11/2018 Haddad .................. G16H 70/20
2019/0231432 A1* 8/2019 Amanatullah ....... A61B 90/361
2020/0405398 A1* 12/2020 Amanatullah ....... G02B 27/017
2022/0287676 A1* 9/2022 Steines .................. A61B 90/37

FOREIGN PATENT DOCUMENTS

WO 2009044287 A2 4/2009
WO 2009076452 A2 6/2009

* cited by examiner

*Primary Examiner* — Bijan Mapar
(74) *Attorney, Agent, or Firm* — Zhong Law, LLC

(57) ABSTRACT

Systems, methods and instrumentalities are described herein for automatically devising and executing a surgical plan associated with a patient in a medical environment, e.g., under the supervision of a medical professional. The surgical plan may be devised based on images of the medical environment captured by one or more sensing devices. A processing device may determine, based on all or a first subset of the images, a patient model that may indicate a location and a shape of an anatomical structure of the patient and determine, based on all or a second subset of the images, an environment model that may indicate a three-dimensional (3D) spatial layout of the medical environment. The surgical plan may be devised based on the patient model and the environment model, and may indicate at least a movement path of a medical device towards the anatomical structure of the patient.

15 Claims, 7 Drawing Sheets

SYSTEMS AND METHODS FOR SURGICAL TASK AUTOMATION

BACKGROUND

Medical procedures (e.g., surgeries) are complicated operations that require concentration, precision, and coordination. Even with the advancement of technologies, these operations are still conducted manually, requiring medical staff to focus on executing protocols and observing conditions of the patient, while also attending to tools and equipment (e.g., lighting, X-ray scanner, surgical robot arm, etc.) and being cognizant of the operating environment in order to ensure that tools and/or equipment are within reach when needed and that the movement of one tool or device does not interfere with the ongoing procedure or collide with other tools or devices in the medical environment. Furthermore, a patient's physical characteristics, positions, and/or movements during a procedure may require continuous adjustments of the parameters, configurations and/or settings of medical devices (e.g., a surgical robot arm) so that they may adapt to the specific conditions of the patient. In light of these complications, attempting to devise and perform a surgical plan manually may have negative effects. For example, it may impose additional burdens on the medical staff, it may produce results that lack accuracy and consistency, and/or it may be difficult to monitor or verify. Accordingly, it is highly desirable to automate surgical planning and execution in a medical environment in order to relieve the burden on medical professionals as well as to enhance the safety, efficiency, and effectiveness of the operations.

SUMMARY

Described herein are systems, methods and instrumentalities associated with automatically devising a surgical plan for a patient within a medical environment. A system as described herein may comprise at least one processor configured to receive images captured by one or more sensing devices (e.g., RGB sensors and/or depth sensors), identify one or more persons (e.g., the patient or a medical professional) and one or more objects (e.g., a medical device) in the received images (e.g., using an artificial neural network such as a convolutional neural network), and determine, based on all or a first subset of the images, a patient model that may indicate a location and a shape of an anatomical structure (e.g., an organ of the patient such as the heart) of the patient in the medical environment. The at least one processor may be further configured to determine, based on all or a second subset of the images, an environment model that may indicate a three-dimensional (3D) spatial layout of the medical environment and devise, based on the patient model and the environment model, a surgical plan for the patient, wherein the surgical plan may include at least a movement path of a medical device towards to the anatomical structure of the patient.

In one or more embodiments, the at least one processor may, based on the automatically devised surgical plan, generate information for controlling the medical device (e.g., at least a part of the medical device) and transmit the information to a receiving device (e.g., a controller of the medical device). In one or more embodiments, the patient model described herein may further indicate a body shape and a pose of the patient, for example, through a 3D human mesh that may be generated based on the images captured by the sensing devices. In one or more embodiments, the patient model may further include a 3D representation (e.g., a 3D point cloud) that indicates the location and shape of the anatomical structure of the patient.

In one or more embodiments, the 3D spatial layout of the medical environment indicated by the environment model may include respective locations or contours of one or more objects and one or more people in the medical environment, the one or more objects including the medical device described herein. In one or more embodiments, the one or more people may include the patient and at least one medical professional, and the environment model may include information that distinguishes the patient from the at least one medical professional. In one or more embodiments, the environment model may include respective 3D representations (e.g., 3D point clouds) associated with the one or more objects in the medical environment, and the 3D representations may indicate the respective locations and shapes of the one or more objects. In one or more embodiments, the at least one processor may be configured to determine at least one of the patient model or the environment model based on a machine-learning (ML) model.

In one or more embodiments, the at least one processor may be further configured to present the surgical plan on a display device, receive a feedback regarding the surgical plan (e.g., from the medical professional), and modify the surgical plan based on the feedback. The at least one processor may be configured to present the surgical plan, for example, by presenting a graphical representation of the anatomical structure of the patient (e.g., overlaid with a 3D human mesh of the patient) and the movement path of the medical device on the display device. In one or more embodiments, the at least one processor may be configured to obtain additional images of the medical environment that may indicate a change associated with the patient model or the environmental model of the medical environment, and update at least one of the patient model or the environment model based on the additional images of the medical environment. In one or more embodiments, the images of the medical environment may include at least one depth image that may indicate respective distances of one or more objects in the medical environment from a view point towards the medical environment.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1:
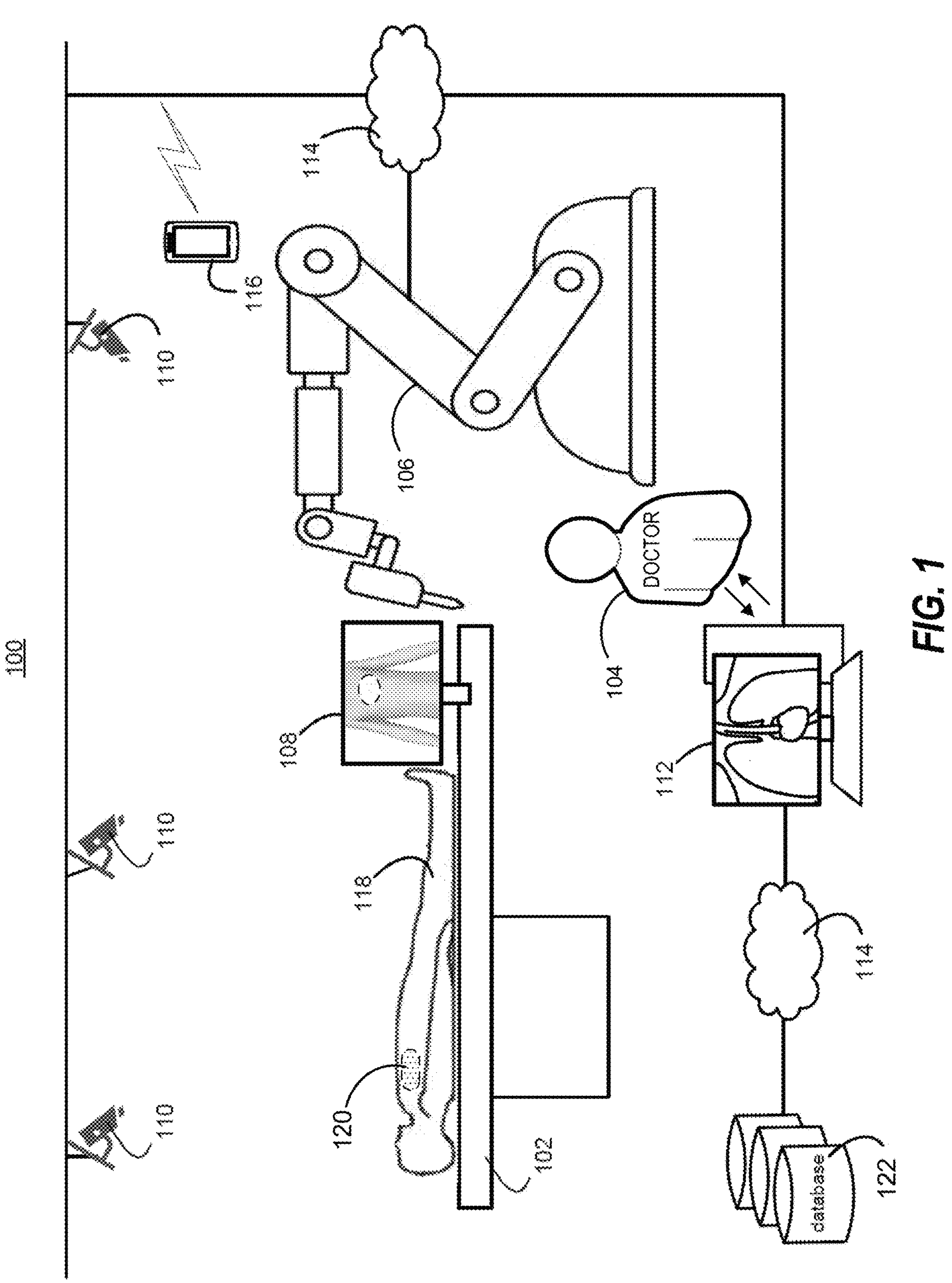
FIG. 1 is a simplified block diagram illustrating an example system associated with automatic surgical planning and execution in accordance with one or more embodiments described herein.

FIG. 1 is a block diagram illustrating an example system described herein that may be used to automatically devise a surgical plan for a patient 118 in a medical environment 100. The medical environment 100 may be any facility in a healthcare setting such as, e.g., an operating room. The medical environment 100 may be equipped with various tools, devices, and/or equipment such as a patient bed 102, a surgical robotic arm 106, a patient monitoring device 108, etc. The tools, devices, and/or equipment may be maneuvered (e.g., manually or automatically) to accommodate the needs of a surgical plan for a medical procedure being performed on patient 118. For example, the patient bed 102 may be raised or lowered, the surgical robotic arm 106 may be manipulated (e.g., moved, tilted, or rotated) towards a specific location (e.g., towards anatomical structure 120), a lighting device (not shown) may be adjusted to focus on a surgical site, etc.

Part or all of the operations in the medical environment 100 may be automated, for example, utilizing one or more sensing devices 110 and/or a processing device 112 (e.g., a computer) communicatively coupled to the one or more sensing devices 110. The sensing devices 110 may be installed at various locations of the medical environment 100 and may be communicatively coupled to the processing device 112 and/or other devices of the medical environment 100 via a communication network 114. Each of the sensing devices 110 may include one or more sensors such as one or more 2D visual sensors (e.g., 2D cameras), one or more 3D visual sensors (e.g., 3D cameras), one or more red, green and blue (RGB) sensors, one or more depth sensors, one or more RGB plus depth (RGB-D) sensors, one or more thermal sensors (e.g., infrared (FIR) or near-infrared (NIR) sensors), one or more motion sensors, one or more radar sensors, and/or other types of image capturing circuitry that may be configured to capture images of a person, an object, or a scene in the medical environment 100. Depending on the type of cameras, sensors, and/or image capturing circuitry included in the sensing devices 110, the images generated by the sensing devices 110 may include, for example, one or more photos, one or more thermal images, one or more radar images, and/or the like. The sensing devices 110 may be configured to generate the images described herein in response to detecting a person (e.g., patient 118), an object (e.g., surgical robotic arm 106), or a scene (e.g., a standing medical professional, such as doctor 104, examining the patient 118 lying on the patient bed 102) in the medical environment 100. The sensing devices 110 may be configured to generate the images described herein based on a preconfigured schedule or time interval, or upon receiving a control signal (e.g., from a remote control device 116) that triggers the image generation.

Each of the sensing devices 110 may include a functional unit (e.g., a processor) configured to control the image capturing functionalities described herein. The functional unit may also be configured to process the images (e.g., pre-process the images before sending the images to processing device 112), communicate with other devices located inside or outside of the medical environment 100, determine a characteristic (e.g., a person or object) of the medical environment 100 based on the captured images, etc. Each of the sensing devices 110 may include a communication circuit and may be configured to exchange information with one or more other sensing devices via the communication circuit and/or the communication network 114. The sensing devices 110 may form a sensor network within which the sensing devices 110 may transmit data to and receive data from each other. The data exchanged between the sensing devices 110 may include, for example, imagery data captured by each sensing device 110 and/or control data for discovering each sensing device's 110 presence and/or calibrating each sensing device's 110 parameters. For instance, when a new sensing device 110 is added to the medical environment 100, the sensing device 110 may transmit messages (e.g., via broadcast, groupcast or unicast) to one or more other sensing devices 110 in the sensor network and/or a controller (e.g., a processing device as described herein) of the sensor network to announce the addition of the new sensing device 110. Responsive to such an announcement or transmission of data, the other sensing devices 110 and/or the controller may register the new sensing device 110 and begin exchanging data with the new sensing device 110.

The sensing devices 110 may be configured to be installed at various locations of the medical environment 100 including, e.g., on a ceiling, above a doorway, on a wall, on a medical device, etc. From these locations, each of the sensing devices 110 may capture images of a person, object or scene that is in the field of view (FOV) of the sensing device 110 (e.g., the FOV may be defined by a viewpoint and/or a viewing angle). The FOV of each of the sensing devices 110 may be adjusted manually or automatically (e.g., by transmitting a control signal to the sensing device) so that the sensing device 110 may take images of a person, an object, or a scene in the medical environment 100 from different viewpoints or different viewing angles.

Each of the sensing devices 110 may be configured to exchange information with other devices (e.g., surgical robotic arm 106) in the medical environment 100, e.g., via the communication network 114. In examples, each of the sensing devices 110 may be configured to transmit the images captured by the sensing device 110 to the processing device 112. In examples, the processing device 112 may be configured to retrieve the images captured by the sensing devices 110 from the sensing devices 110, e.g., via a pull mechanism. The transmission and/or retrieval of images may be performed on a periodic basis or in response to receiving a control signal instructing the transmission or retrieval. For instance, the processing device 112 may be configured to receive a notification from the sensing devices 110 when images are captured and retrieve the image in response to receiving the notification.

The configuration and/or operation of the sensing devices 110 may be at least partially controlled by a programming device 116. For example, the programming device 116 may be configured to initialize and modify one or more operating parameters of the sensing devices 110 including, e.g., the resolution of images captured by the sensing devices 110, a periodicity of data exchange between the sensing devices 110 and the processing device 112, a frame or bit rate associated with the data exchange, a duration of data storage on the sensing devices, etc. The programming device 116 may also be configured to control one or more aspects of the operation of the sensing devices 110 such as triggering a calibration of the sensing devices 110, adjusting the respective orientations of the sensing devices 110, zooming in or zooming out on a person or object in the medical environment 100, triggering a reset, etc. The programming device 116 may be a mobile device (e.g., such a smartphone, a tablet, or a wearable device), a desktop computer, a laptop computer, etc., and may be configured to communicate with the sensing devices 110 and/or the processing device 110 over the communication network 114. The programming device 116 may receive information and/or instructions from a user (e.g., via a user interface implemented on the programming device 116) and forward the received information and/or instructions to the sensing devices 110 via the communication network 114.

The communication network 114 described herein may be a wired or a wireless network, or a combination thereof. For example, the communication network 114 may be established over a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) or 5G network), a frame relay network, a virtual private network (VPN), a satellite network, and/or a telephone network. The communication network 114 may include one or more network access points. For example, the communication network 114 may include wired and/or wireless network access points such as base stations and/or internet exchange points through which one or more devices in the medical environment 100 may be connected to exchange data and/or other information. Such exchange may utilize routers, hubs, switches, server computers, and/or any combination thereof.

The processing device 112 may be configured to receive images from the sensing devices 110 and determine one or more characteristics of the medical environment 100 (e.g., a 3D spatial layout of the medical environment) based on the images. These characteristics may include, for example, people and/or objects that are present in the medical environment 100, and the respective locations (e.g., 3D locations) and/or shapes of the people and/or objects in the medical environment 100. The people presented in the medical environment 100 may include, e.g., a patient 118 and/or medical staff (e.g., the doctor 104, a technician, a nurse, etc.) attending to the patient 118. The objects presented in the medical environment 100 may include, e.g., the surgical robotic arm 106, the monitoring device 108, the patient bed 102, and/or other medical devices or tools not shown in FIG. 1. Based on the determined characteristics of the medical environment 100, the processing device 112 may devise and/or execute a surgical plan including commands for automating one or more aspects of the operations inside the medical environment 100. For example, in response to detecting the people and/or objects in the medical environment 100, and determining the respective locations/shapes of the people and objects, the processing device 112 may generate a surgical plan including one or more messages (e.g., one or more instructions and/or commands) to maneuver at least a part of a target medical device (e.g., such as the surgical robotic arm 106) towards the anatomical structure 120 of the patient 118, e.g., without requiring a physician or a technician to manually manipulate the target medical device. The location of the patient 118 may include a 3D location (e.g., in terms of [X, Y, Z] coordinates) of a scan or surgical site of the patient 118 (e.g., the anatomical structure 120), and the processing device 112 may be configured to transmit the one or more control messages to the target medical device (e.g., to a control unit of the target medical device) via a communications interface such as an application programming interface (API) of the target medical device. The processing device 112 may determine potential obstacles (e.g., other tools or devices in the medical environment 100 such as the monitor device 108) between the patient 118 and the target medical device, and include navigation instructions (e.g., navigation directions and/or step sizes) in the one or more messages generated by the processing unit 112 to prevent the target medical device from colliding with other objects (e.g., such as the monitoring device 108) and/or people (e.g., the doctor 104 attending to the patient 118) in the medical environment 100 while the medical device (e.g., surgical robotic arm 106) moves towards the anatomical structure 120 of the patient 118.

The processing device 112 may be configured to transmit the one or more messages to a receiving device to control the target medical device based on the one or more messages. The receiving device may be the surgical robotic arm 106 itself or a control unit of the surgical robotic arm 106 that may be located inside the surgical robotic arm 106 or remotely from the surgical robotic arm 106 (e.g., in a separate room). The receiving device may be communicatively coupled to the processing device 112, for example, via the communication network 114. The processing device 112 may provide a notification to the receiving device and/or the medical staff attending to the patient 118 regarding the control operation(s) to be performed for the target medical device. For instance, the processing device 112 may devise a surgical plan including an estimate of a movement path of the surgical robotic arm 106 towards the anatomical structure 120 (e.g., the heart) of the patient 118 based on the determined characteristics of the medical environment 100 (e.g., based on respective locations of the people and/or objects detected in the medical environment 100), and provide (e.g., indicate) the estimate to the receiving device and/or the medical staff (e.g., the doctor 104). The estimate may be provided in various forms including, for example, a plot of the movement path or a simulation (e.g., an animated simulation) of the medical device's movements. The estimate may be presented on the monitoring device 108 or another suitable display device such as a display device attached to the processing device 112. The processing device 112 may also be configured to provide a visual representation of the 3D layout of the medical environment 100 based on people and/or objects detected in the images captured by the sensing devices 110. The visual representation may indicate, for example, the people and/or objects detected in the medical environment 100 and/or their respective locations in the medical environment 100. The visual representation may be provided to a receiving device in the medical environment 100 and/or a controller of the medical environment 100 (e.g., a physician or technician, such as doctor 104, supervising the medical environment 100). The medical staff (e.g., the doctor 104) in charge of the medical environment 100 may supervise and/or intervene with the surgical plan devised by the processing device 112. For example, the medical staff may have priority over the processing device 112 with respect to modifying the surgical plan and/or stopping the movement of the robotic arm 106 (e.g., in response to noticing inaccurate or incorrect movements of the robotic arm).

In examples, the processing device 112 may be configured to identify the one or more persons (e.g., the patient 118 or a medical professional, such as the doctor 104) in the medical environment 100 based on an artificial neural network (ANN) trained to implement a first machine learning (ML) model for detecting the one or more persons based on all or a first subset of images captured by the sensing device(s) 110. The processing device 112 may be further configured to determine, based on all or the first subset of images, a patient model that may indicate a pose and/or body shape of the patient as depicted by the images, and/or a location and/or shape of the anatomical structure 120 of the patient 118 (e.g., the heart) that may be the target of a surgical procedure. For instance, the patient model may include one or more 3D representations such as one or more 3D meshes, 3D point clouds, one or more kinematic/skeleton models (e.g., comprising a connected group of human joints), and/or other types of parametric models. A first 3D mesh may indicate the pose and/or body shape of the patient, while a second 3D mesh (or a 3D point cloud) may indicate the location and/or shape of the anatomical structure 120 of the patient (e.g., as described further below with respect to FIG. 2). In examples, the processing device 112 may generate a visualization of the patient model (e.g., including the 3D mesh(es) and/or 3D point cloud(s) described herein), and display it on the monitoring device 108 (e.g., as shown in FIG. 1) such as the doctor 104 may verify and/or modify the surgical plan devised by the processing device 112 based on the display.

In examples, the processing device 112 may be further configured to determine, based on all or a second subset of images captured by the sensing device(s) 110, an environment model that may indicate a 3D spatial layout of the medical environment 100 (e.g., in terms of respective [X, Y, Z] coordinates or locations of the people and objects detected by the processing device based on the images, and/or the respective contours of the people and objects). For instance, the processing device 112 may be configured to determine the respective 3D locations (e.g., including depth information) of the people and objects (e.g., surgical robotic arm 106) based on one or more RGB images and/or one or more depth images captured by the sensing device(s) 110. The RGB images may depict the appearances of the people and objects in the medical environment 100, while the depth images may indicate the depth positions of the people and objects in the medical environment 100. In examples, to determine the location of a person or object in the medical environment 100 based on images of the person or object, the spatial relationship between a coordinate system associated with the medical environment 100 and a coordinate system associated with the images may be established. The coordinate systems may be Cartesian coordinate systems in which the location of a person or object may be defined using respective coordinates of the person or object in X, Y, or Z direction relative to an origin of the coordinate system, but a skilled person in the art will understand that other types of coordinate systems (e.g., such as a cylindrical coordinate system or a spherical coordinate system) may also be used without affecting the functionalities described herein. In examples, multiple RGB sensors (e.g., cameras) may be used to capture images of the person(s) or object(s) in the medical environment, and determine the 3D locations of persons(s) or objects(s) based on the intrinsic and/or extrinsic parameters of the RGB sensors (e.g., which may be obtained during installation of the RGB sensors. In examples, one or more depth sensors may be used and calibrated with the RGB sensors to determine the 3D locations of the person(s) or object(s) based on the respective depth values of the person(s) or object(s) and/or the RGB sensor parameters.

In examples, the one or more people present in the medical environment 100 may include the patient 118 and at least one medical professional (e.g., the doctor 104), and the environment model may include information (e.g., labels or annotations) that distinguishes the patient 118 from the at least one medical professional. This may be accomplished, for example, based on the detected positions of the one or more people in the medical environment such as by determining that a person lying down on the patient bed 102 is the patient 118 and that a person standing up near the patient bed 102 is the medical professional. As another example, point cloud-based or RGB+D (e.g., depth) image based segmentation models may be trained (e.g., learned using a CNN) to delineate the patient 118 and the doctor 104 from an input image, and the same technique may also be used to distinguish different objects in the medical environment.

In examples where human models (e.g., parametric human models) for the one or more people detected in the medical environment are generated, the processing device 112 may generate a more sophisticated model for the patient (e.g., such as a patient model that depicts both the body surface of the patient and an anatomical structure of the patient), and a less sophisticated model for the at least one medical professional (e.g., such as a human model that only depicts a rough body contour of the medical professional). In examples, the environment model may include respective 3D representations such as 3D point clouds of the one or more objects detected in the medical environment 100, and the 3D representations may indicate respective geometric properties of the one or more objects such as, e.g., the 3D locations, shapes, orientations, and/or deformations of the one or more objects in the medical environment 100.

The processing device 112 may devise and/or execute the surgical plan described herein based at least on the patient model and the environment model, where the surgical plan may include at least a movement path of a medical device (e.g., the surgical robotic arm 106) towards the anatomical structure 120 (e.g., the heart) of the patient 118. For example, the processing device 112 may use the patient model to determine a surgical area (e.g., based on the location and shape of the anatomical structure 120 indicated by the patient model) of the patient and generate instructions or commands (e.g., as part of the surgical plan) to move a medical device (e.g., the surgical robotic arm 106, etc.) towards the determined surgical area. The processing unit 112 may also adjust the parameters of the medical device (e.g., incision angels for surgical robotic arm 106, etc.) to better target the surgical area. Alternatively, or in addition, the processing device 112 may indicate the surgical area to a physician (e.g., by highlighting the surgical area on the 3D human mesh displayed on monitoring device 108 and/or on a display of processing unit 112) so that an incision, for example, may be performed with improved accuracy. The processing device 112 may render a visualization (e.g., an augmented or virtual reality visualization) in which the 3D location the anatomical structure 120 may be overlaid with the 3D human mesh of the patient to provide real-time guidance to a physician (e.g., the doctor 104) or technician during a medical procedure. The processing device 112 may generate information for controlling the medical device (e.g., at least a part of the medical device) based on the devised surgical plan, and may transmit the information to a receiving device (e.g., the medical device itself or another control unit like programming device 116) for exercising the control. The processing device 112 may be present the surgical plan on a display device, such as patient monitoring device 108 or a display device of the processing unit 112, receive a feedback regarding the surgical plan (e.g., from a medical professional, such as the doctor 104, via an interface of the processing unit 112), and modify the devised surgical plan based on the feedback. In examples, the processing device 112 may be configured to obtain additional images of the medical environment 100 that indicate a change associated with the patient 118 and/or a change associated with the 3D layout of the medical environment 100, and update at least one of the patient model, the environment model, or the devised surgical plan based on the additional images of the medical environment 100.

In examples, the processing device 112 may be communicatively coupled to a database 122, for example, via the communication network 114. The database 122 may comprise a patient record repository that stores basic information of the patient 118, diagnostic and/or treatment histories of the patient 118, scan images of the patient 118, etc. As a part of the automatically devised surgical plan of a medical procedure for the patient 118, the processing device 112 may be configured to retrieve all or a subset of the medical records of the patient 118 from the database 122, analyze the retrieved medical records in conjunction with other information of the patient 118 gathered or determined by the processing device 112 (e.g., such as the human model described herein), and generate commands and/or information that enables one or more aspects of a surgical plan for a medical procedure to be performed for the patient 118 without human intervention. For example, based on past medical scans of the patient 118, body geometry of the patient 118, and/or other preferences and/or constraints associated with the patient 118, the processing device 112 may automatically determine the parameters and/or configurations of a device (e.g., the position and/or orientation of the surgical robotic arm 106) used in the surgical plan for the medical procedure and cause the parameters and/or configurations to be implemented for the medical device, e.g., by transmitting the parameters and/or configurations to a control unit of the medical device. The processing device 112 may also display, for example, a medical scan associated with the anatomical structure 120 on a display (e.g., as requested by the doctor 104 via an interface of the processing device 112) in order to assist the doctor 104 with the execution of the devised surgical plan.

One or more of the tasks may have been described herein as being initiated and/or implemented by a processing device, such as the processing device 112, in a centralized manner. It should be noted, however, that the tasks may also be distributed among multiple processing devices (e.g., interconnected via the communication network 114, arranged in a cloud-computing environment, etc.) and performed in a distributed manner. Further, even though the processing device 112 may have been described herein as a device separate from the sensing devices (e.g., the sensing devices 110), the functionalities of the processing device 112 may be realized via one or more of the sensing devices (e.g., the one or more sensing devices 110 may comprise respective processors configured to perform the functions of the processing device 112 described herein). Therefore, some embodiments of the present disclosure may not include a separate processing device (e.g., such as processing device 112), and one or more sensing devices (e.g., the sensing devices 110) may assume the responsibilities of the processing device.

Figure 2:
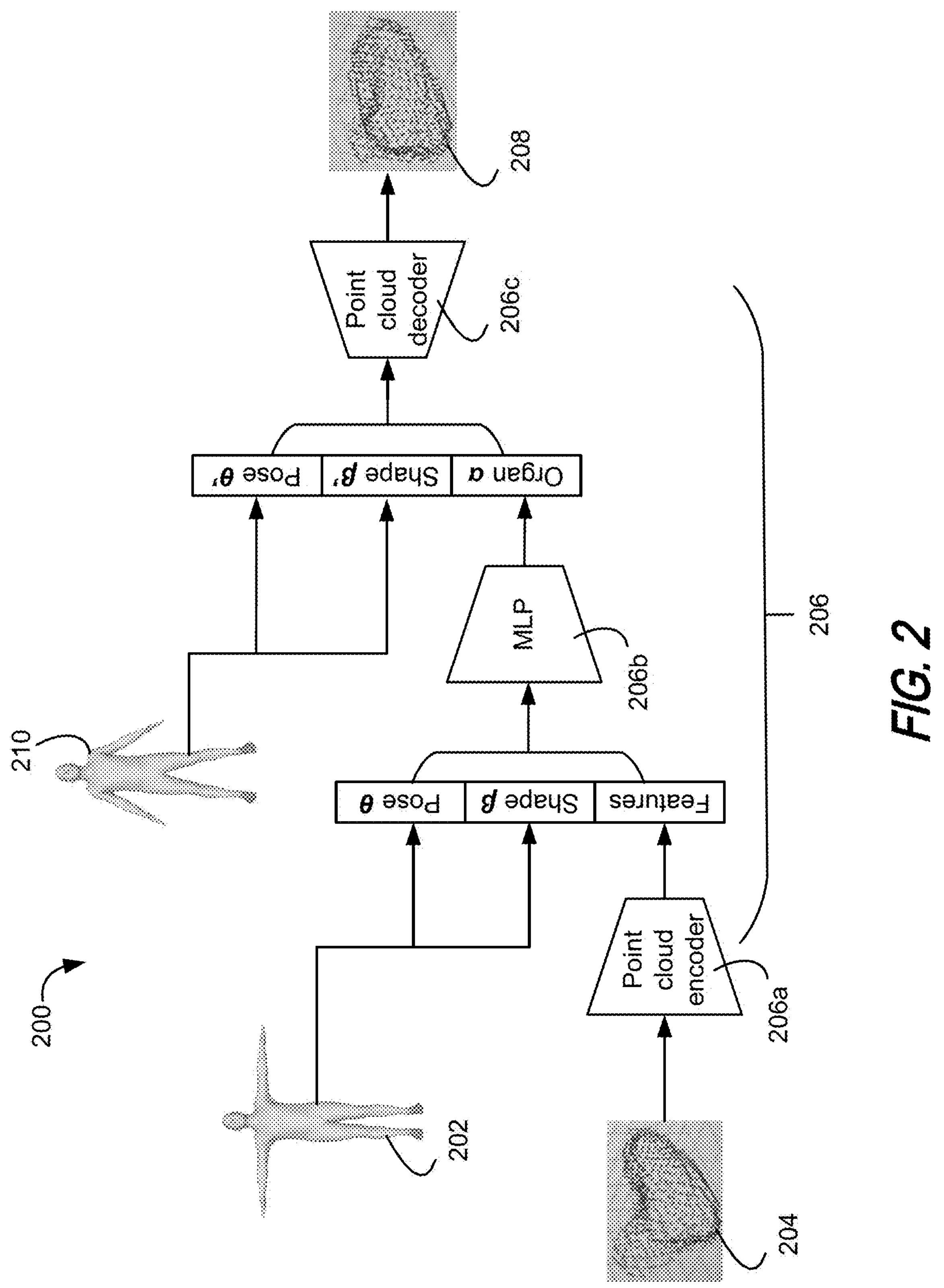
FIG. 2 is a simplified diagram illustrating example operations associated with automatically determining the shape and/or location of an anatomical structure in accordance with one or more embodiments described herein.

At least one of the patient model or the environment model described herein may be determined using machine learning (ML) such as deep learning techniques (e.g., based on pre-trained ML model(s)). FIG. 2 is a simplified diagram illustrating example operations that may be associated with automatically determining the geometric characteristics of an organ or tissue (e.g., anatomical structure 120 of FIG. 1) of a patient based on an ML model. The example operations may be performed by a device or apparatus such as the processing unit 112 or sensing devices 110 shown in FIG. 1, which, for ease of description, may be referred to herein as an organ geometry estimator. As shown by FIG. 2, the organ geometry estimator 200 may be configured to obtain first model 202 of the patient (e.g., the 3D human mesh described with respect to FIG. 1) and a representation 204 of the organ or tissue (e.g., spleen, liver, heart, etc.) of the patient. The first model 202 may include a parametric model of the patient, a two-dimensional (2D) or three-dimensional (3D) contour of the patient, a 3D mesh of the patient, a 3D point cloud representing the body shape and/or pose of the patient, a 2D or 3D skeletal representation of the patient, a descriptor of one or more 2D or 3D joint locations of the patient, a set of measurements indicating the physical characteristics of the patient, and/or other types of representations that may indicate the body shape and/or pose of the patient when the patient is in a certain position (e.g., standing in front of a scanning device, lying on a surgery bed, etc.). Using a parametric model as an example, the first model 202 may include a plurality of parameters such as a plurality of pose parameters $\theta$ (e.g., 72 pose parameters associated with the joints of the patient) and/or a plurality of shape parameters $\beta$ (e.g., 10 coefficients of a principal component analysis (PCA) space) that may be used to determine the body shape and/or pose of the patient (e.g., via a 3D mesh). The first model 202 may be generated by the organ geometry estimator 200 or a different device or apparatus based on images (e.g., RGB images, depth images, thermal images, etc.) of the patient captured by the sensing devices described herein (e.g., sensing devices 110 of FIG. 1). If generated by a device other than organ geometry estimator 200, first model 202 may be provided (e.g., the parameters of first model 202 may be provided) to organ geometry estimator 200 for performing the operations shown in FIG. 2.

The representation 204 shown in FIG. 2 may indicate one or more geometric characteristics (e.g., shape and/or location) of the organ that may correspond to the body shape and/or pose of the patient represented by the first model 202. The representation 204 may be in various forms including, for example, a 3D point cloud of the organ, a parametric model (e.g., a 3D parametric model) of the organ, etc. The representation 204 may be generated, for example, based on one or more scan images of the organ (e.g., taken while the patient is in the body shape and/or pose indicated by the first model 202) and a statistical shape model of the organ. The statistical shape model may include a mean shape of the organ (e.g., a mean point cloud indicating the shape of the organ) and a principal component matrix that may be used to determine the shape of the organ depicted by the one or more scan images (e.g., as a variation of the mean shape) based on features extracted from the one or more scan images. The statistical shape model may be predetermined, for example, based on sample scan images of the organ collected from a certain population or cohort and segmentation masks of the organ corresponding to the sample scan images. The segmentation masks may be registered with each other via affine transformations and the registered segmentation masks may be averaged to determine a mean point cloud representing a mean shape of the organ. Based on the mean point cloud, a respective point cloud may be derived in the image domain for each sample scan image, for example, through inverse deformation and/or transformation. The derived point clouds may then be used to determine a principal component matrix, for example, by extracting the principal modes of variations to the mean shape.

It should be noted that the representation 204 (e.g., a point cloud) may be derived by the organ geometry estimator 200 or by a different device or apparatus. In the latter case, the representation 204 may be provided to the organ geometry estimator 200 for performing the example operations described herein. As shown in FIG. 2, the organ geometry estimator 200 may include an artificial neural network (ANN) 206 trained to determine the correlation (e.g., a spatial relationship) between the geometric characteristics (e.g., shape and/or location) of the organ and the body shape and/or pose of the patient based on model 202 of the patient and representation 204 of the organ. Such a correlation may be represented, for example, through a plurality of parameters (e.g., referred to herein as α) that may indicate how the geometric characteristics of the organ may change in accordance with changes in the patient's body shape and/or pose (e.g., from a first body shape and/or first pose to a second body shape and/or second pose).

In examples, the ANN 206 may include a point cloud feature encoder 206*a* trained to extract features from the representation 204 of the organ. The point cloud feature encoder 206*a* may include a convolutional neural network (CNN) with a plurality of layers such as one or more convolutional layers, one or more pooling layers, and/or one or more fully connected layers. Each of the convolutional layers may include a plurality of convolution kernels or filters configured to extract features from the representation 204. The convolution operations may be followed by batch normalization and/or line or non-linear activation, and the features extracted by the convolutional layers may be down-sampled through the pooling layers and/or the fully connected layers (e.g., using a 2×2 window and a stride of 2) to reduce the redundancy and/or dimension of the features (e.g., by a factor of 2) to obtain a representation of the down-sampled features, for example, in the form of a feature map or feature vector (e.g., a PTC or point cloud vector).

In examples, the ANN 206 may include an encoder 206*b* trained to encode the features of the representation 204 extracted by the point cloud feature encoder 206*a*, the shape parameters β, and/or the pose parameters θ into a plurality of parameters α that may represent the correlation (e.g., a mapping or spatial relationship) between the geometric characteristics (e.g., shape and/or location) of the organ and the body shape or pose of the patient. In examples, the encoder 206*b* may include a multi-layer perception (MLP) neural network with multiple layers (e.g., an input layer, an output layer, and one or more hidden layers) of linearly or non-linearly-activating nodes (e.g., perceptrons) trained to infer the correlation between the geometric characteristics of the organ and the body shape or pose of the patient, and generate parameters α to represent the correlation. In examples, the parameters α may include a vector of floating point numbers (e.g., float32 numbers) that may be used to determine the locations (e.g., coordinates) of one or more points on representation 204 (e.g., in the image domain) based on the locations (e.g., coordinates) of one or more points on the first model 202 (e.g., in the image domain). Subsequently, given a second model 210 of the patient that indicates a new (e.g., different) body shape and/or pose of the patient (e.g., compared to first model 202), the organ geometry estimator 200 may generate (e.g., estimate or predict) the representation 208 (e.g., a point cloud) based on the parameters α to indicate the geometric characteristics (e.g., shape and/or location) of the organ under the new body shape and/or pose indicated by the second model 210.

In examples, ANN 206 may include a point cloud decoder 206*c* trained to generate a representation 208 (e.g., a point cloud) based on the parameters α and model 210 of the patient. In examples, the point cloud decoder 206*c* may include one or more un-pooling layers and one or more transposed convolutional layers. Through the un-pooling layers, the point cloud decoder 206*c* may up-sample the features of point cloud 204 extracted by point cloud encoder 206*a* and encoded by encoder 206*b*, and further process the up-sampled features through one or more transposed convolution operations to derive a dense feature map (e.g., up-scaled from the original feature map produced by point cloud encoder 206*a* by a factor of 2). Based on the dense feature map, the point cloud decoder 206*c* may recover the representation 208 of the organ to reflect changes in the geometric characteristics of the organ (e.g., changes in the shape and/or location of the organ) caused by changes in the body shape and/or pose of the patient as indicated by the second model 210.

Figure 3:
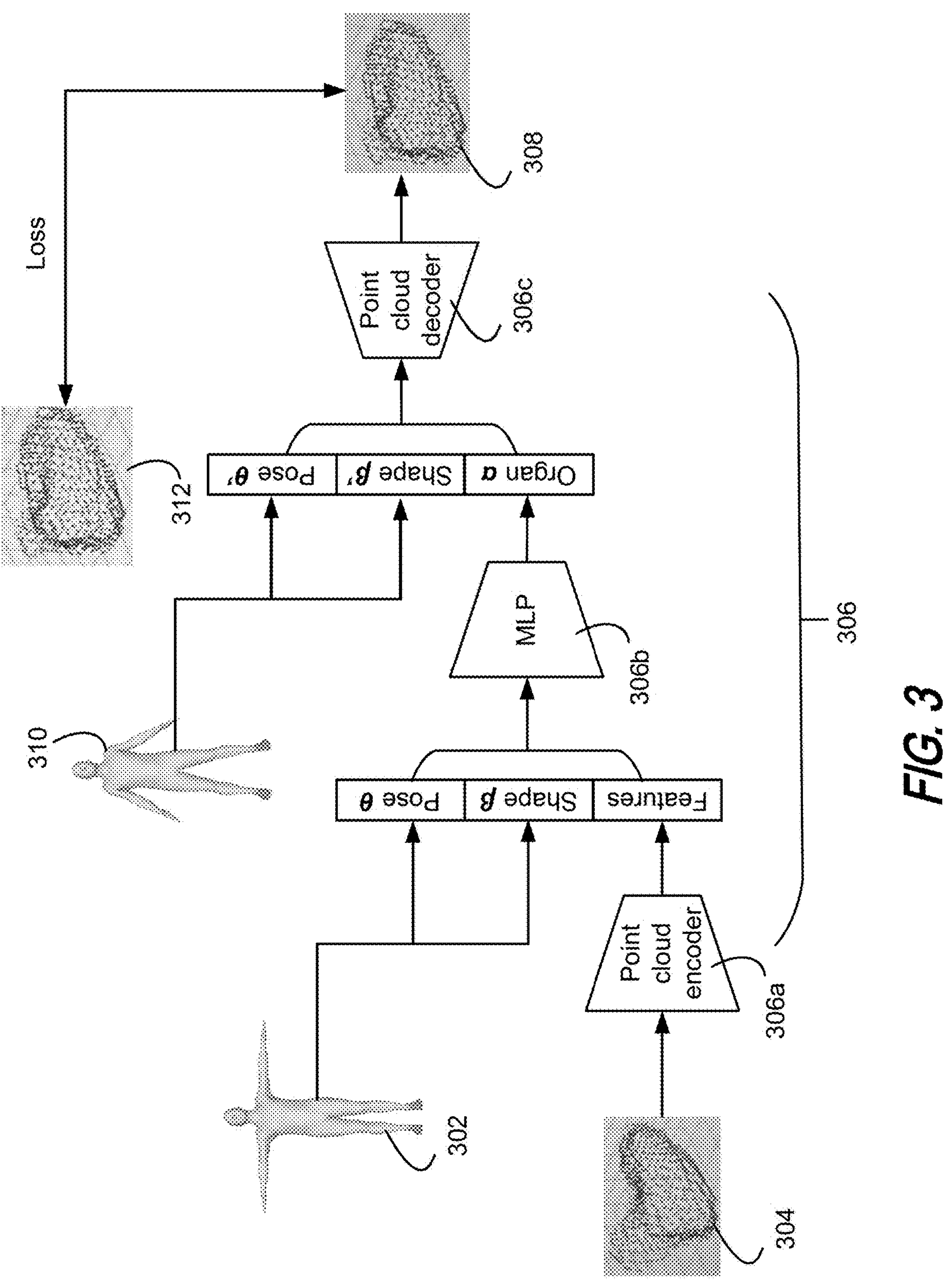
FIG. 3 is a simplified diagram illustrating example operations associated with the training of a neural network to automatically determine the shape and/or location of an anatomical structure in accordance with one or more embodiments described herein.

FIG. 3 is a simplified diagram illustrating an example of training a neural network (e.g., neural network 306, which may be an instance of the ANN 206 shown in FIG. 2) for automatically determining the geometric characteristics (e.g., shape and/or location) of an organ (e.g., anatomical structure 120) based on the body shape and/or pose of a patient (e.g., patient 118 of FIG. 1). The training may be conducted using a plurality of patient models (e.g., parametric human models such as skinned multi-person linear (SMPL) models) and a plurality of representations (e.g., 3D point clouds) of the organ, which may be obtained from publicly available training datasets. Each of the plurality of representations of the organ may be associated (e.g., paired) with a corresponding one of the plurality of patient models (e.g., the training representation may depict the shape and/or location of the organ when the corresponding patient is in the position indicated by the patient model). As described herein, each of the patient models used for the training may include a plurality of pose parameters θ (e.g., 72 pose parameters), a plurality of shape parameters β (e.g., 10 coefficients of a PCA space), and/or a plurality of vertices (e.g., (6890, 3) vertices) that may be derived based on pose parameters θ and shape parameters β. Similarly, each of the representations used for the training may include a plurality of parameters (e.g., (512, 3) vertices of a 3D point cloud) indicating the geometric characteristics (e.g., shape and/or location) of the organ.

During the training process, the neural network 306 may obtain first patient training model 302 and a corresponding first training representation 304 of the organ. Through a point cloud encoder 306*a*, the neural network 306 may extract features from the first training representation 304 and provide the extracted features, together with shape parameters β and pose parameters θ of the first training model 304, to an encoder (e.g., an MLP encoder) 306*b* to estimate the parameters α described herein. As explained above, the parameters α may represent a correlation or mapping (e.g., a spatial relationship) between the geometric characteristics of the organ (e.g., reflected through the representation 304)

and the body shape and/or pose of the patient (e.g., reflected through the first training model 302) in the image space. The neural network 306 may then obtain a second patient training model 310 and a corresponding second training representation 312 of the organ. Using a point cloud decoder 306*c*, the neural network 306 may estimate a representation 308 (e.g., a point cloud) of the organ based on the parameters $\alpha$ predicted by the MLP encoder 306*b* and the shape parameters $\beta'$ and/or pose parameters $\theta'$ of the second training model 310. The neural network 306 may then compare the representation 308 with a second training representation 312 (e.g., a ground truth representation) and determine a loss associated with the encoding and/or decoding operations described above. Such a loss may be determined based on various loss functions including, for example, mean squared errors (MSE), an L1 norm, an L2 norm, a structural similarity index (SSIM), etc. Once the loss is determined, the neural network 306 may adjust its parameters (e.g., the weights associated with the various filters or kernels of the point cloud encoder 306*a*, MLP encoder 306*b*, and point cloud decoder 306*c*) by back-propagating the loss through the neural network 306 (e.g., based on a gradient descent of the loss).

Figure 4:
FIG. 4 is a flow diagram illustrating an example method for automatically devising a surgical plan for a patient in accordance with one or more embodiments described herein.
Figure 4:
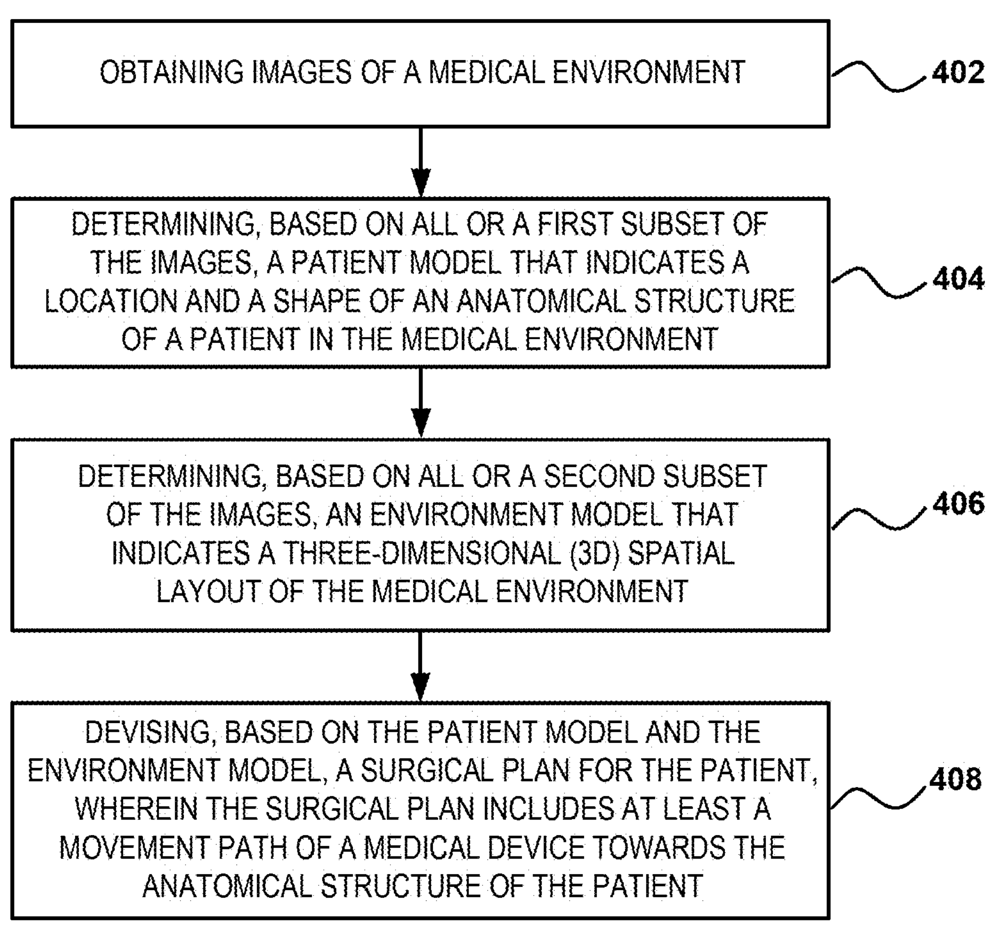

FIG. 4 illustrates an example method 400 that may be performed by a processing device (e.g., the processing device 112) and/or one or more sensing devices (e.g., the sensing devices 110) to automatically devise a surgical plan for a patient (e.g., the patient 118) in a medical environment (e.g., the medical environment 100) in accordance with one or more embodiments described herein. As shown, images of the medical environment 100 may be obtained at 402, for example, by the one or more sensing devices (e.g., which have been installed in the medical environment), and transmitted to the processing device. At 404, responsive to receiving all or a first subset of the captured images, the processing device may, e.g., based on neural network or ML model implemented by the processing device, analyze the images, extract visual features from the images, and determine a patient model that may indicate the geometric characteristics (e.g., location, size, shape, etc.) of an anatomical structure of the patient (e.g., the anatomical structure 120 shown in FIG. 1) that may be the target of a medical procedure. The geometric characteristics of the anatomical structure may be automatically determined, for example, as described above with respect to FIG. 2. At 406, the processing device may, based on all or a second subset of the images, determine an environment model (e.g., of the medical environment 100) that may indicate a three-dimensional (3D) spatial layout of the medical environment. For example, the processing device may identify one or more persons (e.g., patient 118 and/or doctor 104) and/or one or more objects (e.g., surgical robotic arm 106 or other tools, devices, etc.) in the images, and determine characteristics of the medical environment based on the persons and/or objects detected in the images and/or other information about the medical environment that may be acquired by the processing device. The processing device may assemble information from multiple images (e.g., based on motion information indicated in the multiple images) in order to determine the 3D location of a person and/or object. The processing device may determine the 3D location of a person and/or object by utilizing knowledge about the parameters of the sensing devices 110 such as the relative positions of the sensing devices to each other and to the other people and/or objects in the medical environment. For example, the processing device may determine the depth (e.g., a Z coordinate) of a person or object in the medical environment based on two images captured by respective sensing devices, e.g., using a triangulation technique, and/or the camera parameters of the sensing devices.

At 408, the processing device may devise, based on the patient model and the environment model, a surgical plan for the patient, wherein the surgical plan may include at least a movement path of a medical device (e.g., surgical robotic arm 106) towards the anatomical structure of the patient. For example, the processing device may generate information and/or control signals for automating one or more aspects of the operations in the medical environment. For example, the processing device may transmit a message to a receiving device (e.g., a control unit of a medical device) so that the receiving device may control the medical device (e.g., the surgical robotic arm 106) to move towards the anatomical structure of the patient in the medical environment. The message may include location information of the medical device, the patient and/or the anatomical structure of the patient in the medical environment, and/or navigation instructions for the medical device. As another example, the processing device may detect redundant personnel, tools, and/or devices in the medical environment and may report the detection, for example, to a controller of the medical environment such as a doctor. As yet another example, the processing device may perform a time analysis of the operations being conducted in the medical environment and determine a current phase of a medical procedure being performed for a patient. The processing device may then automatically recommend and/or locate tools or medical devices to accommodate the current and/or subsequent phases of the medical procedure according to the devised surgical plan.

The processing device may continuously perform the operations of 402-408, for example, as new sensing devices are added and/or new objects and persons are detected in the medical environment. The processing device may cease performing these operations (e.g., entering an idle state), for example, if the processing device detects no activities in the medical environment and/or if the processing device receives a command to cease the operations (e.g., from the doctor 104).

Figure 5A:
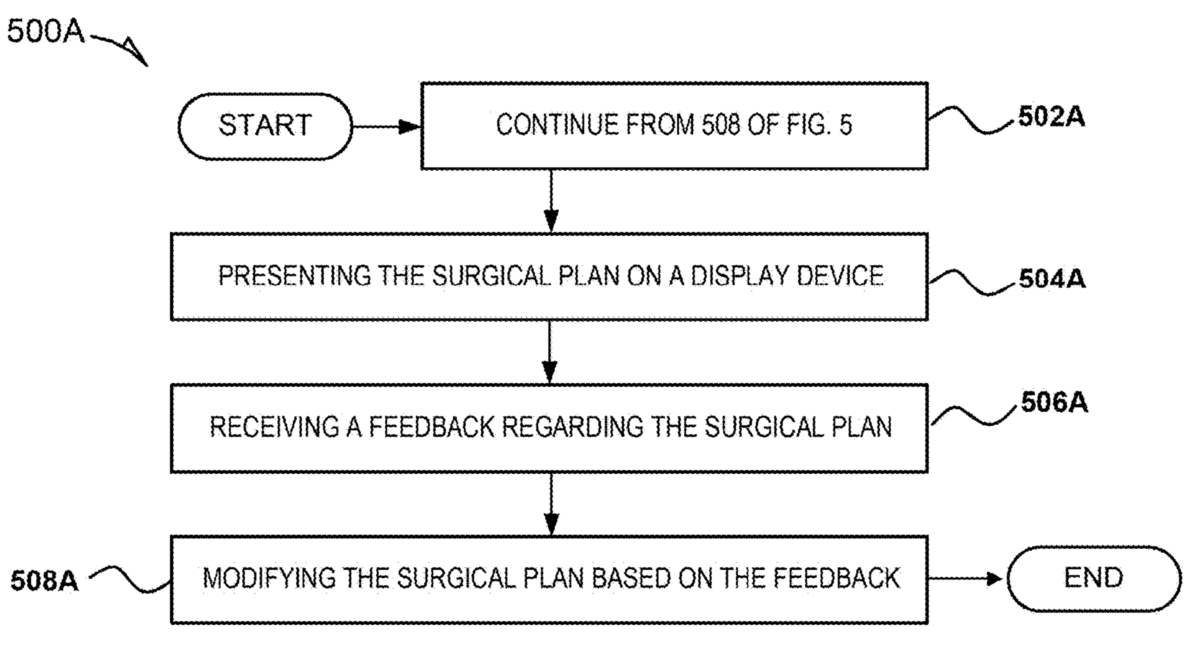
FIG. 5A is a flow diagram illustrating an example method for modifying an automatically devised surgical plan based on received feedback in accordance with one or more embodiments described herein.

FIG. 5A illustrates an example method 500A that may be performed for modifying an automatically devised surgical plan based on received feedback in accordance with one or more embodiments described herein. As shown, the method may, at 502A, continue from operation 408 of method 400 as describe above. At 504A, a devised surgical plan may be presented on a display device. For example, the surgical plan may be displayed on the monitoring device 118 shown in FIG. 1 and/or it may be presented on another display device such as a display device associate with the processing device 112. At 506A, feedback regarding the surgical plan may be received, e.g., from a medical professional in the medical environment such as the doctor 104 via an interface of the processing device 112 or via a control device such as the programming device 116. At 508A, the surgical plan may be modified based on the feedback that was received. For example, the surgical robotic arm 106 shown in FIG. 1 may approach the anatomical structure 120 of the patient 118 at a different incision angle based on the received feedback from doctor 104. The processing device 112 may cease performing these operations (e.g., entering an idle state) and end the method 500A, for example, if the processing device 112 does not receive any further feedback and/or if the processing device 112 receives a command to cease the operations (e.g., from the doctor 104).

Figure 5B:
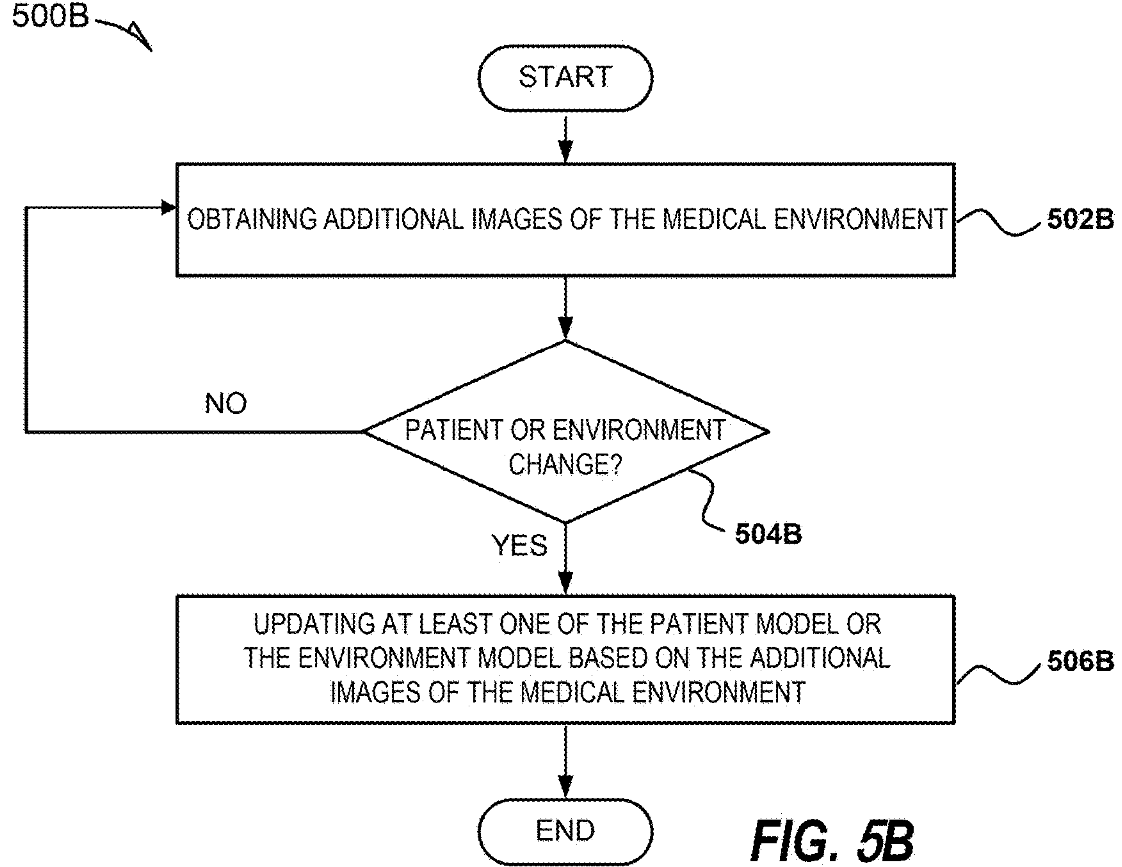
FIG. 5B a flow diagram illustrating an example method for modifying a patient model or an environment model based on receiving additional images in accordance with one or more embodiments described herein.

FIG. 5B illustrates an example method 500B that may be performed for modifying a patient model or an environment model based on receiving additional images in accordance with one or more embodiments described herein. As shown, additional images of the medical environment described herein may be received at 502B, e.g., from one or more sensing devices installed in the medical environment after the patient 118 and/or the surgical robotic arm 106 have moved (e.g., changed their respective X, Y, Z coordinates). At 504B, it may be determined (e.g., by the processing device 112) whether any changes have occurred with regard to the patient 118 and/or the medical environment 100 such as the change of location mentioned above. At 506B, the at least one of the patient model or the environment model may be updated based on the additional images of the medical environment. For example, parameters associated with a 3D mesh of the patient 118 may be updated based on the changes observed in the additional images of the medical environment. The operations illustrated in FIG. 5B may be ended (e.g., the processing device 112 may enter an idle state), for example, if the processing device 112 does not receive any additional images of the medical environment and/or if the processing device 112 receives a command to cease the operations (e.g., from the doctor 104).

Figure 6:
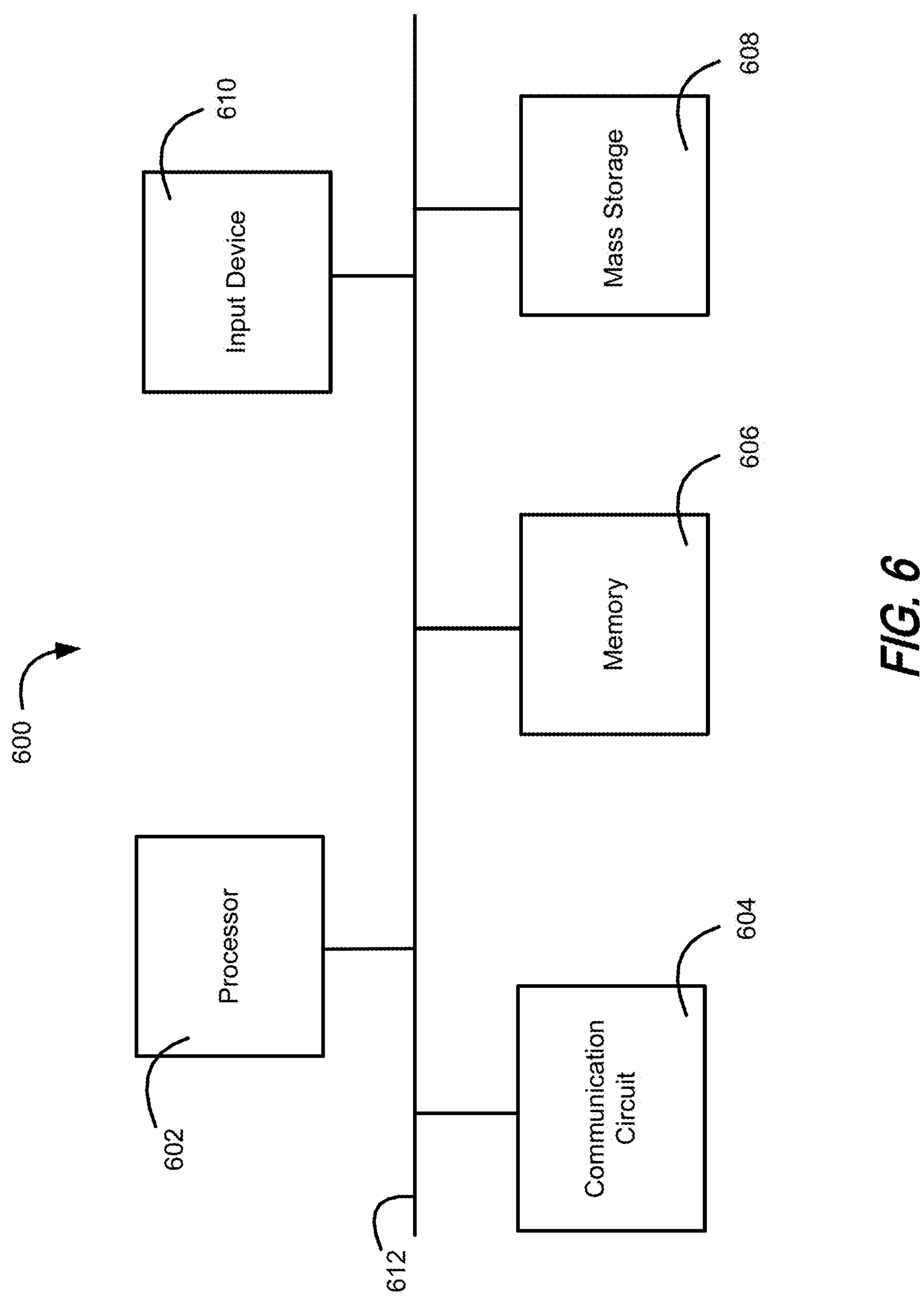
FIG. 6 is a block diagram illustrating example components of an apparatus that may be used to perform one or more of the functions described in accordance with one or more embodiments described herein.

FIG. 6 illustrates example components of an apparatus (e.g., the processing device 112 of FIG. 1) that may be used to perform one or more of the functions described herein. As shown, the apparatus 600 may include a processor 602, which may be a central processing device (CPU), a graphics processing device (GPU), a microcontroller, a reduced instruction set computer (RISC) processor, application specific integrated circuits (ASICs), an application-specific instruction-set processor (ASIP), a physics processing device (PPU), a digital signal processor (DSP), a field programmable gate array (FPGA), or any other circuit or processor capable of executing the functions described herein. The apparatus 600 may further include a communication circuit 604, a memory 606, a mass storage device 608, an input device 610, and/or a communication link 612 (e.g., a communication bus) over which the one or more components shown in FIG. 6 may exchange information. The communication circuit 604 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 606 may include a storage medium configured to store machine-readable instructions that, when executed, cause the processor 602 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 608 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 602. The input device 610 may include a keyboard, a mouse, a voice-controlled input device, a touch sensitive input device (e.g., a touch screen), and/or the like for receiving user inputs to the apparatus 600. The display device 612 may include one or more monitors (e.g., computer monitors, TV monitors, tablets, mobile devices such as smart phones, etc.), one or more speakers, one or more augmented reality (AR) devices (e.g., AR goggles), and/or other accessories configured to facilitate the visual representation of contents a display device (not shown) that may also be part of the apparatus 600. These contents may include, for example, information generated by the processing device such as a 3D mesh of a patient, simulated movements of a medical device, a plot of radiation exposure over time, etc. The display may be rendered in various formats including, for example, videos, animations, and/or AR presentations.

It should be noted that the apparatus 600 may operate as a standalone device or may be connected (e.g., networked or clustered) with other computation devices to perform the functions described herein. And even though only one instance of each component is shown in FIG. 6, a skilled person in the art will understand that the apparatus 600 may include multiple instances of one or more of the components shown in the figure. Furthermore, although example operations of the apparatus may be depicted and described herein in a specific order, the operations may also take place in other orders, concurrently, and/or with other operations not presented or described herein. Not all operations that the apparatus is capable of performing are depicted and described herein, and not all illustrated operations are required to be performed by the apparatus.

Figure 7:
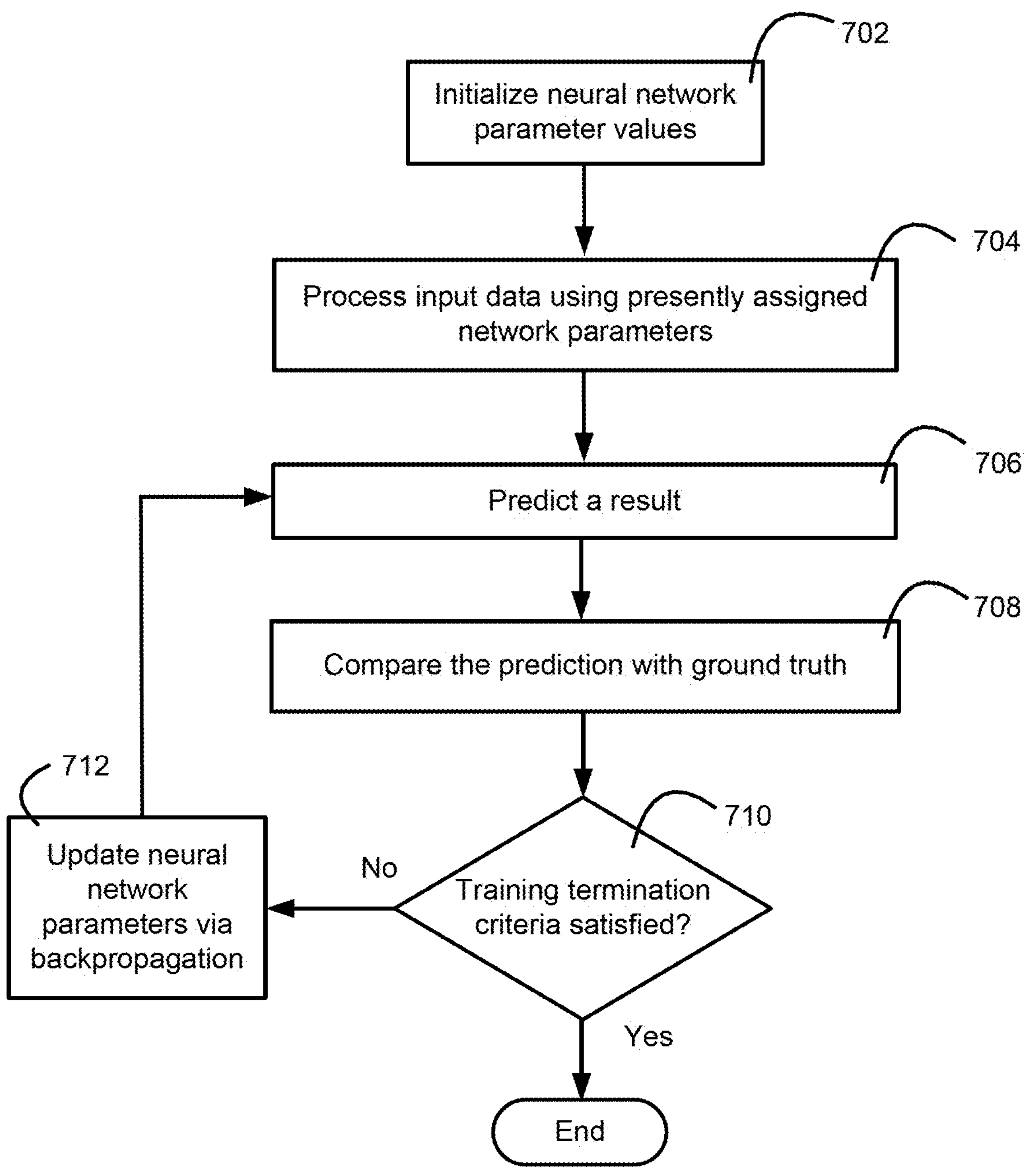
FIG. 7 is a flow diagram illustrating example operations that may be associated with training a neural network to perform one or more of the functions described in accordance with one or more embodiments described herein.

FIG. 7 illustrates an example procedure for training a neural network (e.g., an ML model implemented by the neural network) to perform one or more of the tasks described herein. As shown, the training process may include initializing the operating parameters of the neural network (e.g., weights associated with various layers of the neural network) at 702, for example, by sampling from a probability distribution or by copying the parameters of another neural network having a similar structure. The training process may further include processing an input (e.g., an image captured by the sensing device(s) described herein) using presently assigned parameters of the neural network at 704, and making a prediction for a desired result (e.g., a feature vector, a classification label, etc.) at 706. The prediction result may then be compared to a ground truth at 708 to calculate a loss associated with the prediction based on a loss function such as an MSE, an L1 norm, an L2 norm, etc. The calculated loss may be used to determine, at 710, whether one or more training termination criteria are satisfied. For example, the training termination criteria may be determined to be satisfied if the loss is below a threshold value or if the change in the loss between two training iterations falls below a threshold value. If the determination at 710 is that the termination criteria are satisfied, the training may end; otherwise, the presently assigned network parameters may be adjusted at 712, for example, by backpropagating a gradient descent of the loss function through the network before the training returns to 706.

For simplicity of explanation, the training operations are depicted in FIG. 7 and described herein with a specific order. It should be appreciated, however, that the training operations may occur in various orders, concurrently, and/or with other operations not presented or described herein. Furthermore, it should be noted that not all operations that may be included in the training procedure are depicted and described herein, and not all illustrated operations are required to be performed.

While this disclosure has been described in terms of certain embodiments and associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Other implementations will be apparent to those of skill in the art upon reading and understanding the above description. The scope of the disclosure should, therefore, be determined with reference to the appended claims, along with the full scope of equivalents to which such claims are entitled.

The invention claimed is:

1. An apparatus, comprising:

at least one processor configured to:

obtain images of a medical environment;

determine, based on all or a first subset of the images, a patient model, wherein the patient model includes a three-dimensional (3D) representation of an anatomical structure of a patient in the medical environment, the 3D representation indicating a location and a shape of the anatomical structure, and wherein the patient model further includes a 3D human mesh that indicates a body shape and a pose of the patient;

determine, based on all or a second subset of the images, an environment model that indicates a three-dimensional (3D) spatial layout of the medical environment;

devise, based on the patient model and the environment model, a surgical plan associated with the patient, wherein the surgical plan indicates at least a movement path of a medical device towards the anatomical structure of the patient;

obtain additional images of the medical environment that indicate a change associated with the patient or the 3D spatial layout of the medical environment;

update at least one of the patient model or the environment model based on the additional images of the medical environment; and adjust the surgical plan based on at least one of the updated patient model or the updated environment model.

2. The apparatus of claim 1, wherein the anatomical structure includes an organ of the patient.

3. The apparatus of claim 1, wherein the 3D spatial layout of the medical environment indicated by the environment model includes respective locations or contours of one or more objects and one or more people in the medical environment, the one or more objects including the medical device.

4. The apparatus of claim 3, wherein the one or more people include the patient and at least one medical professional, and wherein the environment model includes information that distinguishes the patient from the at least one medical professional.

5. The apparatus of claim 3, wherein the environment model includes respective 3D representations of the one or more objects in the medical environment, and wherein the respective locations and shapes of the one or more objects are indicated by the 3D representations.

6. The apparatus of claim 1, wherein at least one of the patient model or the environment model is determined using a machine-learning model.

7. The apparatus of claim 1, wherein the at least one processor is further configured to:

present the surgical plan on a display device;

receive a feedback regarding the surgical plan; and modify the surgical plan based on the feedback.

8. The apparatus of claim 7, wherein the at least one processor being configured to present the surgical plan on the display device comprises the at least one processor being configured to present a graphical representation of the anatomical structure of the patient and the movement path of the medical device on the display device.

9. The apparatus of claim 1, wherein the images of the medical environment include at least one depth image that indicates respective distances of one or more objects in the medical environment from a view point towards the medical environment.

10. The apparatus of claim 1, wherein the medical device includes a surgical robotic arm.

11. A method for automating a medical procedure, the method comprising:

obtaining images of a medical environment;

determining, based on all or a first subset of the images, a patient model, wherein the patient model includes a three-dimensional (3D) representation of an anatomical structure of a patient in the medical environment, the 3D representation indicating a location and a shape of the anatomical structure, and wherein the patient model further includes a 3D human mesh that indicates a body shape and a pose of the patient;

determining, based on all or a second subset of the images, an environment model that indicates a three-dimensional (3D) spatial layout of the medical environment;

devising, based on the patient model and the environment model, a surgical plan associated with the patient, wherein the surgical plan includes at least a movement path of a medical device towards the anatomical structure of the patient;

obtaining additional images of the medical environment that indicate a change associated with the patient or the 3D spatial layout of the medical environment;

updating at least one of the patient model or the environment model based on the additional images of the medical environment; and adjusting the surgical plan based on at least one of the updated patient model or the updated environment model.

12. The method of claim 11, wherein the 3D spatial layout of the medical environment indicated by the environment model includes respective locations or contours of one or more objects and one or more people in the medical environment, the one or more objects including the medical device.

13. The method of claim 12, wherein the one or more people include the patient and at least one medical professional, and wherein the environment model includes information that distinguishes the patient from the at least one medical professional.

14. The method of claim 13, wherein the environment model includes respective 3D representations of the one or more objects in the medical environment, and wherein the respective locations and shapes of the one or more objects are indicated by the 3D representations.

15. The method of claim 11, further comprising:
presenting the surgical plan on a display device;
receiving a feedback regarding the surgical plan; and
modifying the surgical plan based on the feedback.

* * * * *